United States Patent [19]

Zink

[11] Patent Number: 5,468,855

[45] Date of Patent: Nov. 21, 1995

[54] BISLACTONES

[75] Inventor: Rudolf Zink, Therwil, Switzerland

[73] Assignee: Ciba-Geigy Corporation, Ardsley, N.Y.

[21] Appl. No.: 298,899

[22] Filed: Aug. 31, 1994

[30] Foreign Application Priority Data

Sep. 9, 1993 [CH] Switzerland ............... 2704/3-8

[51] Int. Cl.$^6$ ............ C07D 417/00; C07D 405/00; C07D 307/83

[52] U.S. Cl. ............ 544/60; 544/150; 544/359; 549/265; 503/220; 546/187; 546/197; 548/517

[58] Field of Search ............... 549/265; 544/60, 544/150, 359; 548/517; 546/187, 197

[56] References Cited

U.S. PATENT DOCUMENTS

| | | | |
|---|---|---|---|
| 3,715,226 | 2/1973 | Lin | 117/36.2 |
| 3,925,416 | 12/1975 | Akamatsu et al. | 260/335 |
| 4,012,419 | 3/1977 | Vincent et al. | |
| 4,938,763 | 7/1990 | Dunn et al. | 604/891.1 |

FOREIGN PATENT DOCUMENTS

| | | |
|---|---|---|
| 0561738 | 9/1993 | European Pat. Off. |
| 2187853 | 1/1974 | France |
| 5-70701 | 3/1993 | Japan |
| 1427318 | 3/1976 | United Kingdom |

OTHER PUBLICATIONS

Chemical Abstracts, vol. 111, No. 18 Oct. 30, 1989, Columbus, Oh., U.S. abstracts No. 16430x.

Derwent Abstract 93-137117/17 af J.P. 05070701 Mar. 1993.

*Primary Examiner*—C. Warren Ivy
*Assistant Examiner*—Amelia Owens
*Attorney, Agent, or Firm*—Kevin T. Mansfield

[57] ABSTRACT

The invention relates to bislactone color formers having improved fastness to sublimation and migration stability, to their preparation, to pressure-sensitive and heat-sensitive recording materials containing said compounds and to their preparation. The novel bislactones have the formula (1) as defined in claim 1.

9 Claims, No Drawings

BISLACTONES

The present invention relates to chromogenic bislactones having improved sublimation fastness and stability to migration, to their preparation and to the use thereof as colour formers in pressure-sensitive or heat-sensitive recording materials, as well as to the preparation of said recording materials.

The bislactones have the general formula (1)

wherein

R$_1$ is hydrogen or C$_1$–C$_4$alkyl;

R$_2$ and R$_3$ are each independently of the other hydrogen; C$_1$–C$_8$alkyl; unsubstituted or C$_1$–C$_4$alkyl- or halogen-substituted C$_4$–C$_7$cycloalkyl; phenyl which is unsubstituted or substituted by C$_1$–C$_4$alkyl, hydroxy or halogen; phenyl-C$_1$–C$_4$alkyl; C$_3$–C$_6$alkenyl; C$_1$–C$_4$alkoxy; C$_1$–C$_4$alkoxy-C$_1$–C$_4$alkyl; 2-tetrahydrofuranyl; or R$_2$ and R$_3$, together with the linking nitrogen atom, are a pyrrolidino, piperidino, morpholino, thiomorpholino or piperazino ring which is unsubstimted or substituted by C$_1$–C$_4$alkyl;

R$_4$ is hydrogen or C$_1$–C$_4$alkyl;

R$_5$ is halogen; nitro; C$_1$–C$_4$alkyl; C$_1$–C$_4$haloalkyl; amino; mono-C$_1$–C$_4$alkylamino; di-C$_1$–C$_4$alkylamino; or COR$_6$;

n is 0; 1; 2; 3; or 4;

R$_6$ is hydrogen; hydroxy; C$_1$–C$_8$alkyl; C$_1$–C$_8$alkoxy; C$_1$–C$_8$haloalkyl; unsubstituted phenyl or phenyl which is substituted by halogen, C$_1$–C$_4$alkyl; C$_1$–C$_4$haloalkyl or C$_1$–C$_4$alkoxy; phenyl-C$_1$–C$_4$alkyl or phenyl-C$_1$–C$_4$alkoxy;

A is —(SO)O— or —(CO)O—;

Q is a saturated or unsaturated aliphatic radical having a molecular weight in the range from 28 to 150, or is a cycloaliphatic or araliphatic radical containing not more than 10 carbon atoms.

In the literature the individual substituent positions at the fluoran ring are numbered differently. In this specification, the following numbering has been adopted:

Within the scope of the above definition, the respective radicals have the following preferred meanings:

Halogen is fluoro, chloro or bromo, preferably fluoro or chloro.

Alkyl within the scope of each definition is straight-chain or branched alkyl. Exemplary alkyl groups are methyl, ethyl, n-propyl, isopropyl, n-butyl, 1-methylbutyl, sec-butyl, tert-butyl, n-pentyl, amyl, isoamyl, n-hexyl, 2-ethylhexyl, n-heptyl, n-octyl, isooctyl, 1,1,3,3-tetramethylbutyl.

Haloalkyl will preferably represent C$_1$–C$_2$haloalkyl radicals such as trichloromethyl, trifluoromethyl, dichlorofluoromethyl, difluorochloromethyl, perchloroethyl, 1,1,2,2-tetrachloroethyl, 1,1,2,2-tetrafluoroethyl, 2,2,2-trichloroethyl. R$_6$ as C$_1$–C$_8$haloalkyl is preferably haloalkyl as defined above and also comprises alkyl radicals in which all, or at least most, of the C—H bonds are replaced by C—Cl or C—F.

Alkoxy is preferably methoxy, ethoxy, n-propoxy, isopropoxy, n-butoxy, isobutoxy, sec-butoxy and tert-butoxy. C$_1$–C$_4$Alkoxy-C$_1$–C$_4$alkyl is preferably methoxymethyl, methoxyethyl, ethoxymethyl or ethoxyethyl.

Mono-C$_1$–C$_5$alkylamino is preferably methylamino, ethylamino, propylamino, butylamino and pentylamino. Di-C$_1$–C$_5$alkylamino comprises both the mixed as well as the corresponding substituted radicals such as methylethylamino, dimethylamino, diethylamino, methylpropylamino, methylbUtylamino, di-n-propylamino, diisopropylamino, di-n-butylamino and di-n-pentylamino and the like.

The phenyl moiety in phenyl-C$_1$–C$_4$alkyl and phenyl-C$_1$–C$_4$alkoxy may be bound via a straight-chain or branched alkyl or alkoxy chain. Phenethyl, benzyl and phenylmethoxy are preferred.

The phenyl moiety of phenyl-C$_1$–C$_4$alkyl, phenyl-C$_1$–C$_4$alkoxy and phenyl itself is preferably unsubstituted or carries up to three identical or different substituents from among those cited.

C$_3$–C$_5$Alkenyl is typically allyl, 1-propenyl or 2-pentenyl, isopropenyl or 2-butenyl. Allyl is preferred. C$_4$–C$_7$Cycloalkyl is cyclobutyl, cycloheptyl, cyclopentyl, cyclohexyl or cycloheptyl. Cyclohexyl is preferred.

Q in the significance of an aliphatic radical is preferably an alkylene group which is unsubstituted or substituted by halogen, preferably chloro. The alkylene group may contain 2 to 8 carbon atoms and be in straight-chain or branched-chain configuration and is preferably the —CH$_2$CH$_2$—, —CH$_2$—CH—, —CH$_2$CH$_2$CH$_2$—,
$\qquad\qquad\qquad\quad$ |
$\qquad\qquad\qquad\quad$ CH$_3$ —CH$_2$CH$_2$CH$_2$CH$_2$—, —CH—CH$_2$CH$_2$—, —CH$_2$—CHCH$_2$—,
$\qquad\qquad\qquad\qquad\quad$ | $\qquad\qquad\qquad\quad$ |
$\qquad\qquad\qquad\qquad\quad$ CH$_3$ $\qquad\qquad\qquad\quad$ CH$_3$ -continued

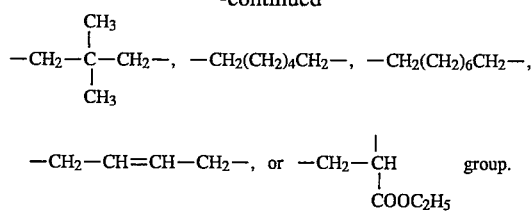

The aliphatic hydrocarbon radical may be interrupted by oxygen atoms and is accordingly the radical of a polyalkylene glycol, for example of a polyethylene glycol, polypropylene glycol or of a polybutylene glycol. Preferably Q is the radical of formula $-(CH_2CH_2O)_mCH_2CH_2-$ or (1a)

$-(CH_2-CHO)_s-CH_2-CH-$ (1b)
$\quad\quad\quad |\quad\quad\quad\quad |$
$\quad\quad\quad CH_3\quad\quad\quad CH_3$ wherein
m is 1 to 9, preferably 1 to 3, and
s is 1 to 5, preferably 1 or 2.

Q in the significance of a cycloaliphatic radical may be the 1,2-cyclopentylene group, the 1,2-cyclohexylene group, the 1,3-cyclohexylene group, the 1,4-cyclohexylene group or

These cycloaliphatic radicals may carry one or two methylene groups.

Q in the significance of an araliphatic radical may be

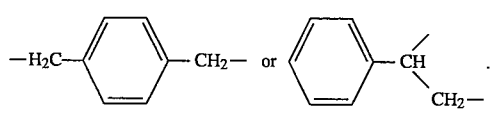

Preferred bislactones of formula (1) are those wherein
$R_1$ is hydrogen or methyl;
$R_2$ and $R_3$ are each independently of the other hydrogen; $C_1$–$C_5$alkyl; or
$R_2$ and $R_3$, together with the linking nitrogen atom, are an unsubstituted or substituted pyrrolidino or piperidino ring;
$R_4$ is hydrogen or methyl;

n is 0; 1; 2; 3; or 4;
$R_5$ is halogen; nitro; $C_1$–$C_4$alkyl; $C_1$–$C_4$haloalkyl; mono-$C_1$–$C_4$alkylamino; di-$C_1$–$C_4$alkylamino; or $COR_6$;
A —(SO)O— or —(CO)O—; and
Q is a saturated or unsaturated aliphatic radical having a molecular weight in the range from 28 to 150, or is a cycloaliphatic or araliphatic radical containing not more than 10 carbon atoms.

Very particularly preferred bislactones of formula (1) are those in which Q is a saturated or unsaturated cycloaliphatic or araliphatic radical, preferably a $C_2$–$C_4$alkylene radical and, most preferably, butylene or ethylene.

Compounds of formula (1) of particular interest are those in which n is 0.

Bislactones which are a major focus of interest are compounds of formula (2)

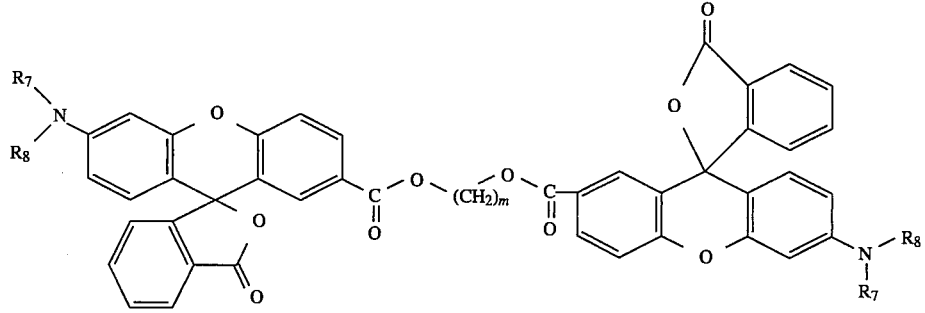

wherein
$R_7$ and $R_8$ are each independently of the other $C_1$–$C_5$alkyl, and m is 1 to 4.

The compounds of formulae (1) and (2) are novel. The process for the preparation of these compounds is carded out by methods which are known per se and comprises reacting 2 mol of the compound of formula

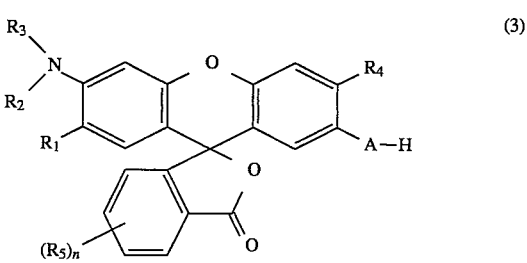

with 1 mol of a dihalo compound of formula

Hal-Q-Hal (4)

wherein
$R_1$, $R_2$, $R_3$, $R_4$, $R_5$, A, Q and n are as defined for formula (1), and Hal is halogen.

Halogen denotes fluoro, chloro and, preferably, bromo.

The process for the preparation of the compounds of formula (1) is also an object of the invention.

The starting compounds of formula (3) are novel, with the exception of 3-diethylamino-7carboxyfluoran. The process for the preparation of these novel compounds comprises reacting a benzophenone of formula (5) with a phenol or phenol ether of formula (6)

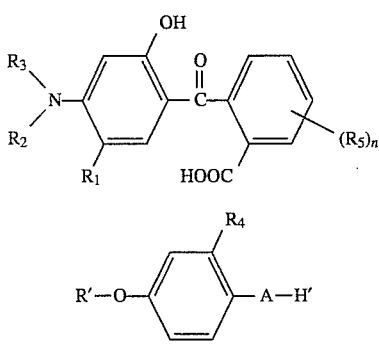

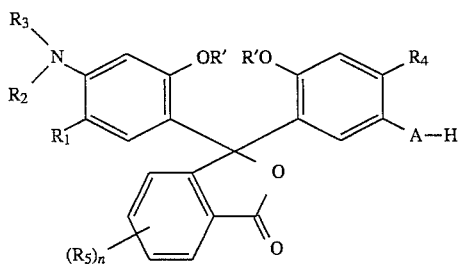

wherein $R_1$ to $R_5$, A and n are as previously defined and

R' is hydrogen or $C_1$–$C_4$alkyl, in the preferred temperature range from 0° to 70° C., in 50 to 100% sulfuric acid, condensing the reaction product to a phthalide of formula and subsequently cyclising the phthalide of formula (7) in the temperature range from 20° to 100° C. to a compound of formula (3).

The compounds of formula (1) are usually colourless or at most faintly coloured. When these sublimation-fast colour formers are brought into contact preferably with an acid developer, i.e. an electron acceptor, then, depending on the meaning of the substituents $R_1$ to $R_6$ and the developer, they produce deep orange to red images. The compounds of formula (I) are also very useful in admixture with one or more other known colour formers, typically 3,3-(bisaminophenyl)phthalides such as CVL, 3-indolyl-3-aminophenylaza- or -diazaphthalides, (3,3-bisindolyl)phthalides, 3-aminofluorans, 3,7-diaminofluorans, 3,7-diamino-6-methylfluorans, 3,6-bisalkoxyfluorans, 3,6-bisdiarylaminofluorans, leukoauramines, spiropyranes, spirodipyranes, chromenopyrazoles, chromenoindoles, phenoxazines, phenothiazines, quinazolines, rhodamine lactams, carbazolyl methanes or other triarylmethaneleuko colorants to give blue, navy blue, grey or black images.

Preferred additional colour formers are those that produce a black image, preferably 3,7-diaminofluorans.

The compounds of formula (I) are used to obtain navy blue, grey or black images together with the other colour formers in a ratio suitable for the desired tinctorial strength. The ratios are also influenced by the developer used in the colour reaction. They can be determined by simple experimentation. It is preferred to use from 10 to 70 % of the bislactone of formula (1) (the percentages are based on the amounts of colour former) in the colour former mixtures. Amounts of about 20 to 50 % are especially preferred. Such mixtures are suitable for reactive copying papers as well as for thermal papers. In the remainder of this specification, the term "colour former" comprises the colour formers of formula (1) as well as the mixtures thereof.

The compounds of formula (1) exhibit an excellent colour intensity and lightfastness on activated clays as well as on phenolic substrates. They are particularly suitable for use as rapidly developing colour formers in a heat-sensitive or, preferably, a pressure-sensitive recording material which may also be a copying material. They are pH-stable and have excellent solubility in the capsule oils. After exposure on a CB sheet they exhibit an insignificant decrease in colour strength (CB decline).

A pressure-sensitive material typically comprises at last one pair of sheets that contains at least one colour former of formula (1) dissolved in an organic solvent, and an electron acceptor as developer.

Typical examples of such developers are active clays such as attapulgite clay, acid clay, bentonite, montmorillonite, activated clay such as acid-activated bentonite or montmorillonite, and also zeolite, halloysite, silica, alumina, aluminium sulfate, aluminium phosphate, zinc chloride, zinc nitrate, zirconium dioxide, activated kaolin or any clay. As developers it is also possible to use acidic organic compounds such as ring-substituted phenols, resorcinols, salicylic acids, including 3,5-bis(α,α-dimethylbenzyl)salicylic acid or 3,5-bis(α-methylbenzyl)salicylic acid or salicylates and their metal salts, e.g. zinc salts, as well as an acidic polymeric material such as a phenolic polymer, an alkyl phenol acetylene resin, a maleic acid rosin resin or a partially or completely hydrolysed polymer of maleic anhydride with styrene, ethylene or vinyl methyl ether, or carboxymethylene. Mixtures of the cited monomers and polymers can also be used. Particularly preferred developers are acid-activated bentonite, zinc salicylates or the condensates of p-substituted phenols with formaldehyde. These last mentioned compounds may also be modified with zinc. Zinc salicylates are disclosed, inter alia, in EP-A-181,283 or DE-A-2,242,250.

The developers may also be used in admixture with other basically inert or substantially inert pigments or with other auxiliaries such as silica gel or UV absorbers, e.g. 2-(2'-hydroxyphenyl)benzotriazoles. Examples of such pigments are: talcum, titanium dioxide, alumina, aluminium hydroxide, zinc oxide, chalk, clays such as kaolin, as well as organic pigments, e.g. urea/formaldehyde condensates (BET surface area: 2–75 $m^2/g$) or melamine/formaldehyde condensates.

The colour former produces a coloured image at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet which is coated with an electron acceptor and a coloured image is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a halogenated paraffin, benzene or diphenyl, for example chloroparaffin, trichlorobenzene, monochlorodiphenyl, dichlorodiphenyl or trichlorodiphenyl, and also esters such as tricresyl phosphate, di-n-butyl phthalate, dioctyl phthalate, trichloroethylphosphate, an aromatic ether such as benzylphenyl ether, a hydrocarbon oil such as paraffin or kerosene, aromatic hydrocarbons, an alkylated derivative (e.g. containing isopropyl, isobutyl, sec- or tert-butyl groups) of diphenyl, naphthalene or terphenyl; dibenzyl toluene, partially hydrogenated terphenyl, mono- to tetra-$C_1$–$C_3$alkylated diphenylalkanes, dodecylbenzene, benzylated xylenes, phenyl xylyl ethane or other chlorinated or hydrogenated condensed aromatic hydrocarbons. Mixtures of different solvents, especially mixtures of paraffin oils or kerosene and diisopropylnaphthalene or partially hydrogenated terphenyl, are often used to obtain optimum solubility of the colour formers, a rapid and intense coloration, and a viscosity which is advantageous for the microencapsulation. For the encapsulation, the novel phthalides are distinguished by the feature that they are readily soluble and are pH-resistant in a pH range from 4 to 10.

The capsule walls can be formed evenly around the droplets of the colour former solution by coacervation. The encapsulating material is described e.g. in U.S. Pat. No. 2,800,457. The capsules may also be conveniently formed from an aminoplast or a modified aminoplast by polycondensation, as described in British patent specifications 989 264, 1 156 725, 1 301 052 and 1 355 124. Microcapsules which are formed by interfacial polymerisation are also suitable, e.g. capsules formed from polyester, polycarbonate, polysulfonamide, polysulfonate, but preferably from polyamide or polyurethane.

The microcapsules containing the colour formers of formula (1) can be used for the production of a wide variety of known kinds of pressure-sensitive copying material. The various systems differ substantially from one another in the arrangement of the capsules, of the colour reactants, and of the support.

The colour formers of formula I can be used with advantage as mixture components in microencapsulated colour former systems. The sublimation fastness of the bislactones of formula (1) is in this connection particularly advantageous. As mentioned at the outset, the bislactones of the prior art exhibit more of a sublimation or migration tendency than the other colour formers used in such mixtures. The mixture ratio must therefore take into account the properties of the component that has the most pronounced sublimation tendency. In contradistinction thereto, the sublimation fastness of the compounds of this invention matches that of the other mixture components. The advantages accruing therefrom are obvious: when choosing the mixture components it is no longer necessary to take special account of more readily sublimable components of the colour former system. The enhancement of migration stability in the novel colour former mixtures has a particularly advantageous effect on the developed image. Even after prolonged storage of the copying material, the image retains its sharp outlines and does not become blurred.

A preferred arrangement is that in which the encapsulated colour former is in the form of a layer on the back of a transfer sheet and the electron acceptor (colour developer) is in the form of a layer on the face of a receiver sheet. Another arrangement of the components is that wherein the microcapsules which contain the colour former, and the developer, are in or on the same sheet in the form of one or more individual layers, or the developer is incorporated in the support.

The capsules are preferably secured to the support by means of a suitable binder. As paper is the preferred support, these binders are principally paper-coating agents such as gum arabic, polyvinyl alcohol, hydroxymethyl cellulose, casein, methyl cellulose, dextrin, starch or starch derivatives or polymer latices. These latter are typically butadiene/styrene copolymers or acrylic homopolymers or copolymers.

The paper employed comprises not only normal paper made from cellulose fibres, but also paper in which the cellulose fibres are replaced (partially or completely) by synthetic polymer fibres. The support may also be a plastic sheet.

The copying paper may also comprise a capsule-free layer that contains the colour former and a colour developing layer wherein the colour developer containing at least one inorganic metal salt of a polyvalent metal, preferably a halide or nitrate such as zinc chloride, tin chloride, zinc nitrate or a mixture thereof.

The compounds of formula (1) may also be used as colour formers in a thermoreactive recording material. This recording material usually comprises at least one support, one or more than one colour former, one electron acceptor, and optionally also a binder and/or wax. If desired, the recording material may also comprise an activator or sensitiser.

The colour formers of formula ( 1 ) may be used with advantage as mixture components in thermoreactive colour former systems. The storage stability (hot and/or moist) and the low background discolouration of the novel bislactones are particularly advantageous.

Thermoreactive recording systems comprise, for example, heat-sensitive recording or copying materials and papers. These systems are used e.g. for recording information, for example in electronic computers, teleprinters or telewriters, or in recording and measuring instruments, e.g. electrocardiographs. The image formation (marking) can also be effected manually with a heated pen. Laser beams can also be used to produce heat-induced images.

The composition of the thermoreactive recording material may be such that the colour former is dispersed or dissolved in one binder layer and the developer is dissolved or dispersed in the binder in a second layer. Another possibility comprises dispersing both the colour former and the developer in one layer. By means of heat the layer or layers are softened at specific areas and the desired colour develops at once at those areas where heat is applied.

Suitable developers are the same electron acceptors as are used in pressure-sensitive papers. Examples of developers are the clays and phenolic resins already mentioned, or also the phenolic compounds disclosed e.g. in German Offenlegungsschrift 1 251 348, for example 4-tert-butylphenol, 4-phenylphenol, methylene bis(p-phenylphenol), 4-hydroxydiphenyl ether, α-naphthol, β-naphthol, methyl or benzyl 4-hydroxybenzoate, 4-hydroxydiphenylsulfone, 4-hydroxy-4'-methyldiphenylsulfone, 4'-hydroxy-4-isopropoxydiphenylsulfone, 4,4'-cyclohexylidenediphenol, 4,4'-isopropylidenediphenol, 4,4'-isopropylidene-bis(2-methylphenol), an antipyrine complex of zinc thiocyanate, a pyridine complex of zinc thiocyanate, 4,4'-bis(hydroxyphenyl)valeric acid, hydroquinone, pyrogallol, phloroglucinol, p-, m- and o-hydroxybenzoic acid, hydroxyphthalic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

It is preferred to use fusible, film-forming binders for making the thermoreactive recording material. These binders are usually water-soluble, whereas the colour formers and the developer are sparingly soluble or insoluble in water. The binder should be able to disperse and fix the colour former and the developer at room temperature.

When heated, the binder softens or melts, so that the colour former comes in contact with the developer and a colour is able to form. Examples of binders which are soluble, or at least swellable, in water are hydrophilic polymers such as polyvinyl alcohol, polyacrylic acid, hydroxyethyl cellulose, methyl cellulose, carboxymethyl cellulose, polyacrylamide, polyvinyl pyrrolidone, gelatin, starch or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose and polyvinyl carbazole. The preferred arrangement, however, is that in which the colour former and the developer are contained in one layer in a water-soluble binder.

To ensure the stability of the heat-sensitive recording material or the density of the developed image, the material may be provided with an additional protective layer. Such a protective layer will normally consist of water-soluble and/ or water-insoluble resins which are conventional polymeric materials or aqueous emulsions of these polymeric materials.

The thermoreactive layers and resin coatings may contain further auxiliaries. To improve the degree of whiteness, to facilitate the printing of papers, and to prevent the heated pen from sticking, these layers may contain e.g. talcum, titanium dioxide, zinc oxide, alumina, aluminium hydroxide, calcium carbonate (e.g. chalk), clays or also organic pigments, for example urea/formaldehyde polymers. To effect the colour formation only within a limited temperature range it is possible to add substances such as urea, thiourea, diphenyl thiourea, acetamide, acetanilide, benzene sulfanilide, stearamide, bis(stearoyl)ethylenediamine, phthalic anhydride, metal stearates such as zinc stearate, phthalonitrile, dimethyl terephthalate, dibenzyl terephthalate or other appropriate fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

A further utility of the compounds of formula (I) is the formation of a coloured image by means of the photocurable microcapsules described e.g. in German Offenlegungsschrift 3 247 488.

The invention is illustrated by the following Examples in which, unless otherwise indicated, percentages are by weight.

Preparation of the novel bislactones

EXAMPLE 1

80 g of the water-moist product of formula

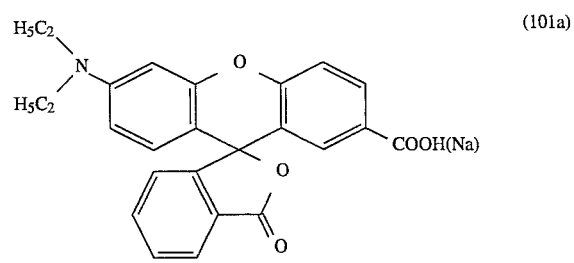

(101a)

(0.05 mol in 100 ml of toluene), 10 g of sodium carbonate and 0.5 g of tetrabutylammonium bromide are dried azeotropically in a water separator. Then 5.4 g (0.025 mol) of 1,4-dibromobutane are added and the mixture is stirred for 16 hours at 80° C., giving the product of formula ( 101 )

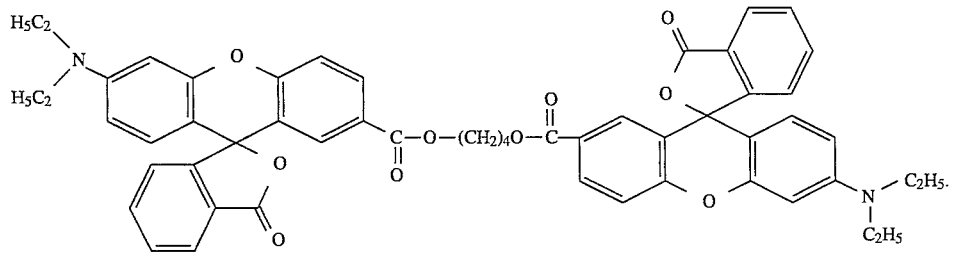

For working up, the toluene solution is clarified by filtration, the toluene is removed by distillation and the residue is recrystallised from a mixture of 8 parts of isopropanol and 5 parts of toluene.

Yield: 9 g of a virtually pure product having a melting point of 105°–110° C.

EXAMPLES 2 to 8

The following compounds listed in Table 1 are obtained in general accordance with the procedure described in Example 1:

TABLE 1

Compounds of the general formula

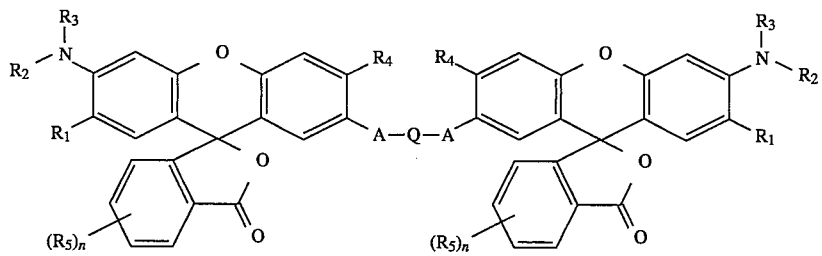

| Example/compound of formula | | $R_1$ | $R_2$ | $R_3$ | $R_4$ | $R_5$ | A | Q |
|---|---|---|---|---|---|---|---|---|
| 2 | (102) | $CH_3$ | $CH_3$ | $CH_3$ | H | n = 0 | $CO_2$ | $-CH_2-CH_2-$ |
| 3 | (103) | H | $C_2H_5$ | $C_2H_5$ | H | n = 0 | $CO_2$ | $-n-(CH_2)_4-$ |
| 4 | (104) | H | $C_4H_9$ | $C_4H_9$ | H | n = 0 | $CO_2$ | $-CH_2CH=CHCH_2-$ |
| 5 | (105) | H | H | $C_2H_5$ | H | n = 0 | $CO_2$ | $-CH_2-CH_2-$ |
| 6 | (106) | H | $C_6H_5$ | H | H | n = 0 | $CO_2$ | $-n-(CH_2)4-$ |
| 7 | (107) | H | $C_2H_5$ | $C_2H_5$ | H | n = 0 | $SO_2$ | $-n-(CH_2)4-$ |
| 8 | (108) | H | ⟨N-⟩ | | H | n = 0 | $SO_2$ | $-CH_2-CH_2-$ |

USE EXAMPLES

EXAMPLE 9

A solution of 1 g of the bislactone of formula (101) in 80 g of diisopropylnaphthalene and 19 g of kerosene is encapsulated by coacervation in a manner known per se with gelatin and gum arabic. The microcapsules are mixed with starch solution and coated on a sheet of paper. The face of a second sheet of paper is coated with activated clay as colour developer. The first sheet containing the sublimation-fast colour former and the sheet coated with the developer are laid on top of each other with the coated sides face to face. Pressure is exerted on the first sheet by writing by hand or by typewriter and a deep orange copy of excellent fastness to light and sublimation develops immediately on the sheet coated with the developer.

EXAMPLE 10

In a ball mill, 32 g of 4,4'-isopropylidenediphenol (bisphenol A), 3.8 g of the distearylamide of ethylenediamine, 39 g of kaolin, 20 g of an 88 % hydrolysed polyvinyl alcohol and 500 ml of water are milled to a particle size of c. 5 μm. In a second ball mill, 2 g of the compound of formula (101 ), 4 g of 3-diethylamino-7-n-octylaminofluoran and 3.3 g of 88 % hydrolysed polyvinyl alcohol as well as 60 ml of water are milled to a particle size of c. 3 μm.

Both dispersions are mixed and coated to a dry coating weight of 0.5 g/m², based on the colour former, on a sheet of paper.

Black writing develops when the dried paper is written on in a commercially available facsimile machine (®Infotec 6510). The paper exhibits no background discolouration.

What is claimed is:

1. A bislactone of formula (1)

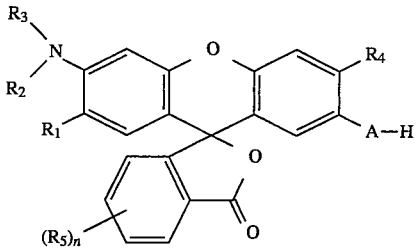

(3)

wherein $R_1$ is hydrogen or $C_1-C_4$alkyl;

$R_2$ and $R_3$ are each independently of the other hydrogen; $C_1-C_8$alkyl; unsubstituted or $C_1-C_4$alkyl- or halogen-substituted $C_4-C_7$cycloalkyl; phenyl which is unsubstituted or substituted by $C_1-C_4$alkyl, hydroxy or halogen; phenyl-$C_1-C_4$alkyl; $C_3-C_6$alkenyl; $C_1-C_4$alkoxy; $C_1-C_4$alkoxy-$C_1-C_4$alkyl; 2-tetrahydrofuranyl; or $R_2$ and $R_3$, together with the linking nitrogen atom, are a pyrrolidino, piperidino, morpholino, thiomorpholino or piperazino ring which is unsubstituted or substituted by $C_1-C_4$alkyl;

$R_4$ is hydrogen or $C_1-C_4$alkyl;

$R_5$ is halogen; nitro; $C_1-C_4$alkyl; $C_1-C_4$haloalkyl; amino; mono-$C_1-C_4$alkylamino; di-$C_1-C_4$alkylamino; or $COR_6$;

n is 0; 1; 2; 3; or 4;

$R_6$ is hydrogen; hydroxy; $C_1-C_8$alkyl; $C_1-C_8$alkoxy; $C_1-C_8$haloalkyl; unsubstituted phenyl or phenyl which is substituted by halogen, $C_1-C_4$alkyl, $C_1-C_4$haloalkyl or $C_1-C_4$alkoxy; phenyl-$C_1-C_4$alkyl or phenyl-$c_1-C_4$alkoxy;

A is $-(SO)O-$ or $-(CO)O-$;

Q is a saturated or unsaturated aliphatic radical having a molecular weight in the range from 28 to 150, or is a cycloaliphatic or araliphatic radical containing not more than 10 carbon atoms.

2. A bislactone of formula (1) according to claim 1, wherein

R$_1$ is hydrogen or methyl;

R$_2$ and R$_3$ are each independently of the other hydrogen; C$_1$–C$_5$alkyl; or R$_2$ and R$_3$, together with the linking nitrogen atom, are an unsubstituted or substituted pyrrolidino or piperidino ring;

R$_4$ is hydrogen or methyl;

n is 0; 1; 2; 3; or 4;

R$_5$ is halogen; nitro; C$_1$–C$_4$alkyl; C$_1$–C$_4$haloalkyl; mono-C$_1$–C$_4$alkylamino; di-C$_1$–C$_4$aklylamino; or COR$_6$ A —(SO)O— or —(CO)O—, and Q is a saturated or unsaturated aliphatic radical having a molecular weight in the range from 28 to 150, or is a cycloaliphatic or araliphatic radical containing not more than 10 carbon atoms.

3. A bislactone of formula (1) according to claim 1, wherein Q is a saturated or unsaturated aliphatic or cycloaliphatic radical.

4. A bislactone according to claim 3, wherein Q is C$_2$–C$_4$alkylene.

5. A bislactone according to claim 1, wherein n is 0.

6. A bislactone according to claim 1 of formula (2)

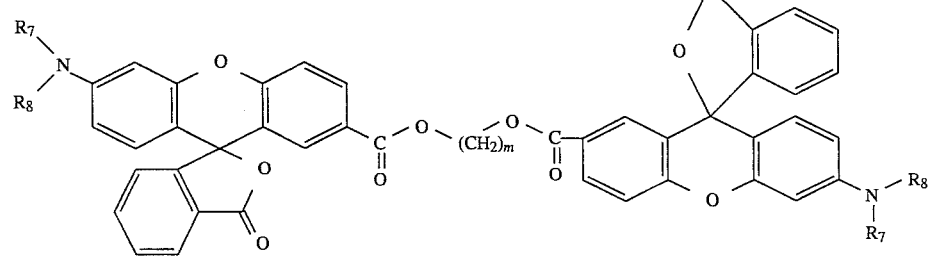

wherein

R$_7$ and R$_8$ are each independently of the other C$_1$–C$_5$alkyl, and m is 1 to 4.

7. A process for the preparation of a bislactone of formula (1), which comprises reacting 2 mol of the compound of formula

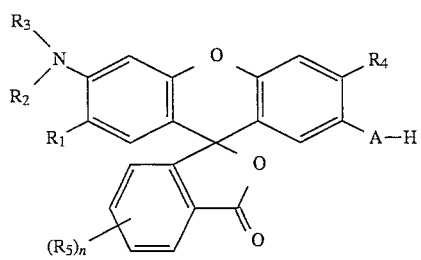

with 1 mol of a dihalo compound of formula

Hal-Q-Hal (4)

wherein

R$_1$, R$_2$, R$_3$, R$_4$, R$_5$, A, Q and n are as defined for formula (1), and Hal is halogen.

8. A compound of formula

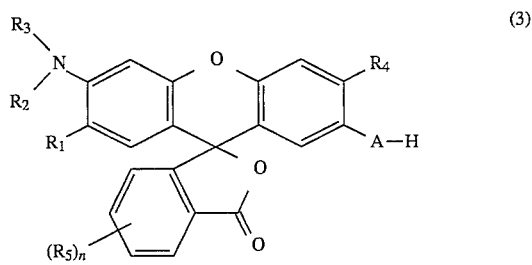

wherein

R$_1$, R$_2$, R$_3$, R$_4$, R$_5$, A, Q and n are as defined for formula (1) in claim 1, with the proviso that 3-diethylamino-7-carboxyfluoran is excluded.

9. A process for the preparation of a compound of formula (3), which comprises reacting a benzophenone of formula (5) with a phenol or phenol ether of formula (6)

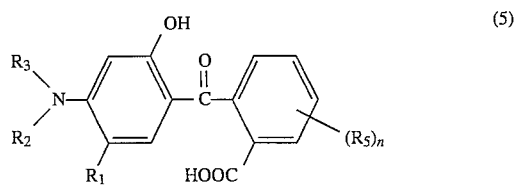

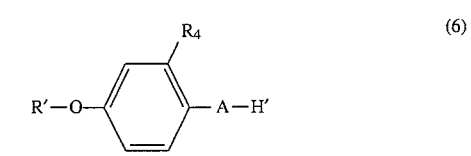

wherein R$_1$ to R$_5$ and n are as previously defined and R' is hydrogen or C$_1$–C$_4$alkyl, in the preferred temperature range from 0° to 70° C., in 50 to 100 % sulfuric acid, condensing the reaction product to a phthalide of formula

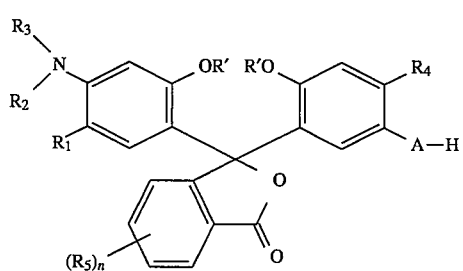 (7)
and subsequently cyclising said phthalide of formula (7) in the temperature range from 20° to 100° C. to a compound of formula (1).
* * * * *

UNITED STATES PATENT AND TRADEMARK OFFICE
CERTIFICATE OF CORRECTION

PATENT NO. : 5,468,855
DATED : November 21, 1995
INVENTOR(S) : Rudolf Zink

It is certified that error appears in the above-identified patent and that said Letters Patent is hereby corrected as shown below:

Column 12, Claim 1, lines 30-40, should read:

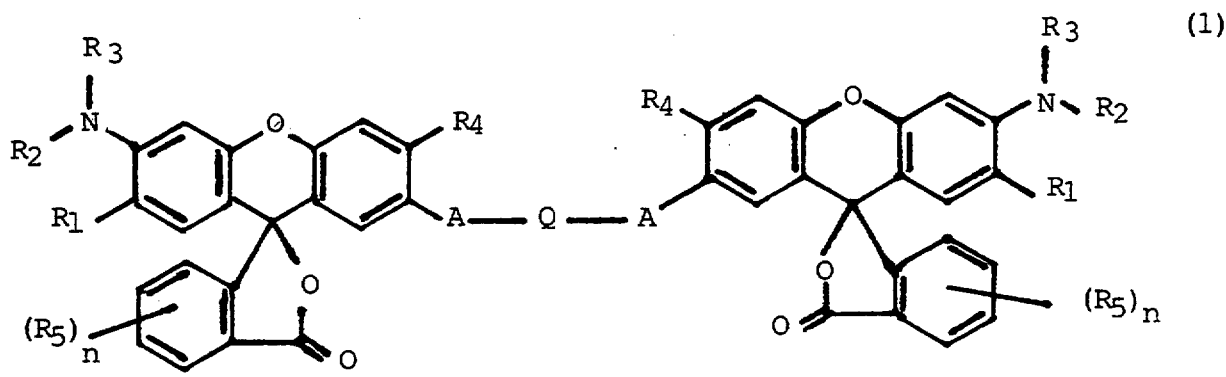

Signed and Sealed this

Thirtieth Day of July, 1996

Attest:

BRUCE LEHMAN

Attesting Officer     Commissioner of Patents and Trademarks